United States Patent
Fischer et al.

(10) Patent No.: US 9,868,713 B2
(45) Date of Patent: *Jan. 16, 2018

(54) CATALYST SYSTEM FOR OXIDIZING O-XYLOL AND/OR NAPHTHALENE INTO PHTHALIC ANHYDRIDE

(71) Applicant: BASF SE, Ludwigshafen (DE)

(72) Inventors: Nico F. Fischer, Heidelberg (DE); Diana C. Galeano Nunez, Mannheim (DE); Michael Krämer, Katzweiler (DE); Markus Schubert, Ludwigshafen (DE); Jürgen Zühlke, Speyer (DE); Hans-Martin Allmann, Neunkirchen (DE)

(73) Assignee: BASF SE (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/119,238

(22) PCT Filed: Feb. 17, 2015

(86) PCT No.: PCT/EP2015/053267
§ 371 (c)(1),
(2) Date: Aug. 16, 2016

(87) PCT Pub. No.: WO2015/121483
PCT Pub. Date: Aug. 20, 2015

(65) Prior Publication Data
US 2017/0008866 A1    Jan. 12, 2017

(30) Foreign Application Priority Data
Feb. 17, 2014  (EP) .................................... 14155332

(51) Int. Cl.
| | | |
|---|---|---|
| *C07D 307/89* | (2006.01) | |
| *B01J 35/00* | (2006.01) | |
| *B01J 23/18* | (2006.01) | |
| *B01J 23/22* | (2006.01) | |
| *B01J 27/198* | (2006.01) | |
| *B01J 35/02* | (2006.01) | |
| *B01J 8/06* | (2006.01) | |
| *C01G 30/00* | (2006.01) | |

(52) U.S. Cl.
CPC ............. *C07D 307/89* (2013.01); *B01J 8/06* (2013.01); *B01J 23/18* (2013.01); *B01J 23/22* (2013.01); *B01J 27/198* (2013.01); *B01J 35/0006* (2013.01); *B01J 35/023* (2013.01); *C01G 30/005* (2013.01); *B01J 2208/06* (2013.01); *B01J 2523/00* (2013.01); *C01P 2002/60* (2013.01)

(58) Field of Classification Search
CPC ................................................... C01G 30/005
See application file for complete search history.

(56) References Cited

U.S. PATENT DOCUMENTS

| | | |
|---|---|---|
| 6,586,361 B1 | 7/2003 | Heidemann et al. |
| 2007/0060758 A1 | 3/2007 | Storck et al. |
| 2009/0306409 A1 | 12/2009 | Gückel et al. |
| 2014/0018550 A1* | 1/2014 | Altwasser et al. ..... B01J 27/198 549/248 |

FOREIGN PATENT DOCUMENTS

| | | | |
|---|---|---|---|
| CN | WO 2012014154 A1 * | 2/2012 | ............. B01J 23/18 |
| DE | 40 06 935 A1 | 9/1991 | |
| DE | 4329907 A1 | 3/1995 | |
| DE | 19839001 A1 | 3/2000 | |
| EP | 522871 A1 | 1/1993 | |
| EP | 1636161 A1 | 3/2006 | |
| WO | WO-2004103943 A1 | 12/2004 | |
| WO | WO2012014154 A1 * | 2/2012 | |
| WO | WO-2012014154 A1 | 2/2012 | |
| WO | WO-2015/121485 | 8/2015 | |

OTHER PUBLICATIONS

International Search Report for PCT/EP2015/053267 dated Jun. 10, 2015.
International Search Report for PCT/EP2015/053270 dated Jun. 16, 2015.
Schubert, U.-A., et al., "Possible effects of site isolation in antimony oxide-modified vanadia/titania catalysts for selective oxidation of o-xylene", Topics in Catalysts, vol. 15, No. 2-4, (2001), pp. 195-200.
Golunski, "Antimony Oxides: a Guide to Phase Changes During Catalyst Preparation", *Applied Catalysis*, vol. 48, pp. 123-135 (1989).

* cited by examiner

Primary Examiner — Noble Jarrell
Assistant Examiner — John S Kenyon
(74) Attorney, Agent, or Firm — Drinker Biddle & Reath LLP

(57) ABSTRACT

The present invention relates to a catalyst system for oxidation of o-xylene and/or naphthalene to phthalic anhydride (PA), comprising a plurality of catalyst zones arranged in succession in the reaction tube, which have been produced using antimony trioxide comprising a noticeable proportion of senarmontite wherein some of the primary crystallites have a size of less than 200 nm. The present invention further relates to a process for gas phase oxidation, in which a gas stream comprising at least one hydrocarbon and molecular oxygen is passed through a catalyst system which comprises a plurality of catalyst zones arranged in succession in the reaction tube and which has been produced using an antimony trioxide comprising a noticeable proportion of senarmontite wherein some of the primary crystallites have a size of less than 200 nm.

10 Claims, 1 Drawing Sheet

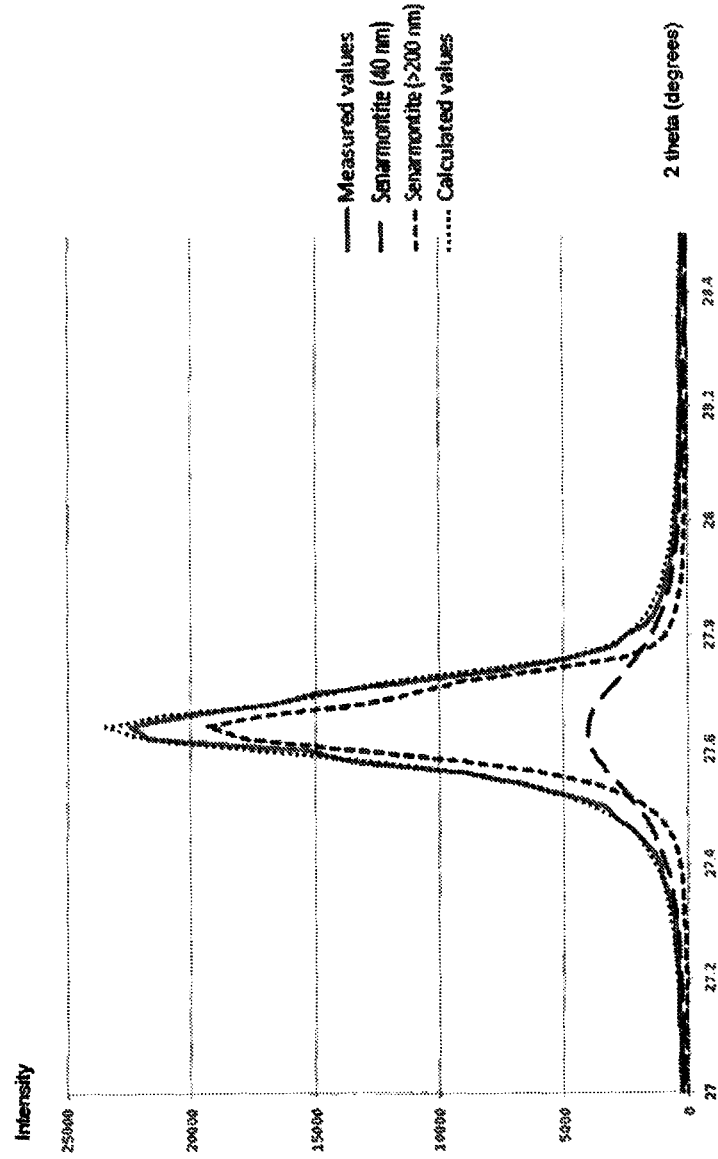

CATALYST SYSTEM FOR OXIDIZING O-XYLOL AND/OR NAPHTHALENE INTO PHTHALIC ANHYDRIDE

CROSS-REFERENCE TO RELATED APPLICATIONS

This application is a national stage application (under 35 U.S.C. §371) of PCT/EP2015/053267, filed Feb. 17, 2015, which claims benefit of European Application No. 14155332.1, filed Feb. 17, 2014, both of which are incorporated herein by reference in their entirety.

The present invention relates to a catalyst system for oxidation of o-xylene and/or naphthalene to phthalic anhydride (PA), comprising a plurality of catalyst zones arranged in succession in the reaction tube, which have been produced using antimony trioxide comprising a noticeable proportion of senarmontite wherein some of the primary crystallites have a size of less than 200 nm. The present invention further relates to a process for gas phase oxidation, in which a gas stream comprising at least one hydrocarbon and molecular oxygen is passed through a catalyst system which comprises a plurality of catalyst zones arranged in succession in the reaction tube and which has been produced using an antimony trioxide comprising a noticeable proportion of senarmontite wherein some of the primary crystallites have a size of less than 200 nm.

A multitude of carboxylic acids and/or carboxylic anhydrides is prepared industrially by the catalytic gas phase oxidation of hydrocarbons such as benzene, the xylenes, naphthalene, toluene or durene in fixed bed reactors. In this way, it is possible to obtain, for example, benzoic acid, maleic anhydride, phthalic anhydride, isophthalic acid, terephthalic acid or pyromellitic anhydride. In general, a mixture of an oxygen-containing gas and the starting material to be oxidized is passed through tubes in which there is disposed a bed of a catalyst. For temperature regulation, the tubes are surrounded by a heat carrier medium, for example a salt melt.

Useful catalysts for these oxidation reactions have been found to be what are called coated catalysts, in which the catalytically active material has been applied in the form of a shell on an inert support material such as steatite. In general, the catalysts have an active material which has been applied in the form of a shell with essentially homogeneous chemical composition. In addition, it is also possible for two or more different active materials to be applied successively to a support. In that case, the reference is made to a two-shell or multi-shell catalyst (see, for example, DE 19839001 A1).

The catalytically active constituents used in the catalytically active material of these coated catalysts are generally titanium dioxide and vanadium pentoxide. In addition, small amounts of a multitude of other oxidic compounds which influence the activity and selectivity of the catalyst as promoters may be present in the catalytically active material, including cesium oxides, phosphorus oxides and antimony oxides.

Catalysts having a particularly high PA yield can be obtained according to EP 1636161 when particular $V_2O_5/Sb_2O_3$ ratios are established and the antimony trioxide has a defined median particle size.

In this case, the presence of antimony oxides leads to an increase in PA selectivity, the cause of which is considered to be isolation of the vanadium centers. The antimony oxides used in the active material of the catalysts may comprise different antimony(III), antimony(IV) and/or antimony(V) compounds; usually, antimony trioxide or antimony pentoxide is used. EP 522871 describes the use of antimony pentoxide; US 2009/306409 and EP 1636161 disclose the use of antimony trioxide.

Compared to antimony tetroxide and antimony pentoxide, antimony trioxide has the property of spreading better on titanium dioxide, such that a significantly better distribution on the catalyst is achieved. Typically, the antimony trioxide used is single-phase senarmontite (cf. Schubert, U.-A. et al., Topics in Catalysis, 2001, vol. 15(2-4), pages 195 to 200). As well as cubic senarmontite, there is also an orthorhombic polymorph of antimony trioxide, called valentinite (Golunski, S. E. et al., Appl. Catal., 1989, vol. 48, pages 123 to 135).

There is a constant need for catalysts for gas phase oxidations having a maximum conversion combined with high selectivity.

It was an object of the present invention to develop a catalyst for the oxidation of o-xylene and/or naphthalene to phthalic anhydride, which enables, at a low salt bath temperature, a high phthalic anhydride yield combined with a low o-xylene and phthalide content.

This object is achieved by a catalyst system for oxidation of o-xylene and/or naphthalene to phthalic anhydride, comprising a plurality of catalyst zones arranged in succession in the reaction tube, which has been produced using an antimony trioxide comprising a noticeable proportion of senarmontite wherein some of the primary crystallites have a size of less than 200 nm.

The invention therefore provides a catalyst system for oxidation of o-xylene and/or naphthalene to phthalic anhydride, comprising a plurality of catalyst zones arranged in succession in the reaction tube, which is produced using an antimony trioxide having a senarmontite content of at least 20% by weight and where the senarmontite primary crystallites have a polymodal size distribution, wherein between 10% and 80% by weight have a primary crystallite size of <200 nm and a median primary crystallite size of <150 nm.

A BRIEF DESCRIPTION OF THE FIGURE

FIG. 1 shows an example of calculated and measured senarmontite peaks at 2 theta=27.7° in an x-ray powder diffractogram, and simulated values for primary crystallite sizes of 40 nm and >200 nm.

The antimony trioxide having the above-described properties which is to be used in accordance with the invention can be used for production of one or more catalyst zones. In a preferred embodiment of the invention, the catalyst system has three, four or five zones, at least one zone having been produced using antimony trioxide having the above-described properties.

In a further preferred embodiment of the invention, the antimony trioxide used for production of the inventive catalyst system has a senarmontite content of at least 50% by weight.

In a further preferred embodiment of the invention, the senarmontite primary crystallites in the antimony trioxide used for production of the inventive catalyst system have a bimodal size distribution.

In a particularly preferred embodiment of the invention, between 10% and 80% by weight of the senarmontite primary crystallites in the antimony trioxide used for production of the inventive catalyst system have a primary crystallite size of <200 nm and a median primary crystallite size of <100 nm, most preferably of <50 nm.

In a further preferred embodiment of the invention, between 10% and 50% by weight of the senarmontite primary crystallites in the antimony trioxide used for production of the inventive catalyst system have a primary crystallite size of <200 nm and a median primary crystallite size of <150 nm.

In a very particularly preferred embodiment of the invention, between 10% and 50% by weight of the senarmontite primary crystallites in the antimony trioxide used for production of the inventive catalyst system have a primary crystallite size of <200 nm and a median primary crystallite size of <100 nm, especially <50 nm.

The inventive catalyst systems can also be used, for example, for avoidance of high hotspot temperatures in conjunction with suitable upstream and/or downstream beds and together with intermediate zones, where the upstream and/or downstream beds and the intermediate zones may generally consist of catalytically inactive or less active material.

The inventive catalysts are generally what are called coated catalysts, in which the catalytically active material has been applied in the form of a shell to an inert support material.

The inert support materials used may be virtually all prior art support materials, as used advantageously in the production of coated catalysts for the oxidation of aromatic hydrocarbons to aldehydes, carboxylic acids and/or carboxylic anhydrides, for example quartz ($SiO_2$), porcelain, magnesium oxide, tin dioxide, silicon carbide, rutile, alumina ($Al_2O_3$), aluminum silicate, steatite (magnesium silicate), zirconium silicate, cerium silicate or mixtures of these support materials. The catalyst supports can be used, for example, in the form of spheres, rings, tablets, spirals, tubes, extrudates or chippings. The dimensions of these catalyst supports correspond to those of catalyst supports used customarily for production of coated catalysts for the gas phase reactions of aromatic hydrocarbons. Preference is given to using steatite in the form of spheres having a diameter of 3 to 6 mm or of rings having an external diameter of 5 to 9 mm and a length of 3 to 8 mm and a wall thickness of 1 to 2 mm.

The inventive catalysts comprise a catalytically active material which comprises, as well as antimony trioxide, at least also vanadium oxide and titanium dioxide, and can be applied to the support material in one or more shells. Different shells may differ in their composition.

Preferably, the catalytically active material, based on the total amount of the catalytically active material, comprises 1% to 40% by weight of vanadium oxide, calculated as $V_2O_5$, and 60% to 99% by weight of titanium dioxide, calculated as $TiO_2$. In preferred embodiments, the catalytically active material may additionally comprise up to 1% by weight of a cesium compound, calculated as Cs, up to 1% by weight of a phosphorus compound, calculated as P, and up to 10% by weight of antimony oxides, calculated as $Sb_2O_3$. All figures for the composition of the catalytically active material are based on the calcined state thereof, for example after calcination of the catalyst at 450° C. for one hour.

Typically, titanium dioxide in the anatase modification is used for catalytically active material. The titanium dioxide preferably has a BET surface area of 15 to 60 $m^2/g$, especially 15 to 45 $m^2/g$, more preferably 13 to 28 $m^2/g$. The titanium dioxide used may consist of a single titanium dioxide or a mixture of titanium dioxides. In the latter case, the value for the BET surface area is determined as the weighted mean of the contributions of the individual titanium dioxides. The titanium dioxide used consists, for example, advantageously of a mixture of a $TiO_2$ having a BET surface area of 5 to 15 $m^2/g$ and a $TiO_2$ having a BET surface area of 15 to 50 $m^2/g$.

Suitable vanadium sources are particularly vanadium pentoxide or ammonium metavanadate. Suitable antimony sources are various antimony trioxides, and an antimony trioxide having a senarmontite content of at least 20% by weight is used as described above in accordance with the invention. Useful phosphorus sources include especially phosphoric acid, phosphorous acid, hypophosphorous acid, ammonium phosphate or phosphoric esters, and in particular ammonium dihydrogenphosphate. Useful sources of cesium include the oxide or hydroxide or the salts which can be converted thermally to the oxide, such as carboxylates, especially the acetate, malonate or oxalate, carbonate, hydrogencarbonate, sulfate or nitrate.

As well as the optional additions of cesium and phosphorus, small amounts of a multitude of other oxidic compounds which influence the activity and selectivity of the catalyst as promoters, for example by lowering or increasing the activity thereof, may be present in the catalytically active material. Examples of such promoters include the alkali metals, more particularly (excluding cesium, which has been mentioned) also lithium, potassium and rubidium, which are usually used in the form of their oxides or hydroxides, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony tetroxide, antimony pentoxide and cerium oxide.

In addition, among the promoters mentioned, useful additives preferably also include the oxides of niobium and tungsten in amounts of 0.01% to 0.50% by weight, based on the catalytically active material.

The shell(s) of the coated catalyst are appropriately applied by spray application of a suspension of $TiO_2$ and $V_2O_5$, which optionally comprises sources of the abovementioned promoter elements, to the fluidized support. Before the coating, the suspension is preferably stirred for a sufficiently long period, for example 2 to 30 hours, especially 12 to 25 hours, to break up agglomerates of the suspended solids and to obtain a homogeneous suspension. The suspension typically has a solids content of 20% to 50% by weight. The suspension medium is generally aqueous, for example water itself or an aqueous mixture with a water-miscible organic solvent such as methanol, ethanol, isopropanol, formamide and the like.

In general, organic binders are added to the suspension, preferably copolymers, advantageously in the form of an aqueous dispersion, of acrylic acid/maleic acid, vinyl acetate/vinyl laurate, vinyl acetate/acrylate, styrene/acrylate and vinyl acetate/ethylene. The binders are commercially available as aqueous dispersions having a solids content of, for example, 35% to 65% by weight. The amount of such binder dispersions used is generally 2% to 45% by weight, preferably 5% to 35% by weight, more preferably 7% to 20% by weight, based on the weight of the suspension.

The support is fluidized in, for example, a fluidized bed apparatus in an ascending gas stream, especially air. The apparatuses usually consist of a conical or spherical vessel in which the fluidizing gas is introduced from the bottom or from the top through an immersed tube. The suspension is sprayed into the fluidized bed via nozzles from the top, at the side or from below. It is advantageous to use a riser tube arranged centrally or concentrically around the immersed tube. Within the riser tube, there is a higher gas velocity which transports the support particles upward. Within the outer ring, the gas velocity is only slightly above the fluidization velocity. Thus, the particles are moved vertically in a circular manner. A suitable fluidized bed apparatus is described, for example, in DE-A 4006935.

In the coating of the catalyst support with the catalytically active material, coating temperatures of 20 to 500° C. are generally employed, and the coating can be effected under atmospheric pressure or under reduced pressure. In general, the coating is effected at 0° C. to 200° C., preferably at 20 to 150° C., especially at 60 to 120° C.

The shell thickness of the catalytically active material is generally 0.02 to 0.2 mm, preferably 0.05 to 0.15 mm. The active material content in the catalyst is typically 5% to 25% by weight, usually 7% to 15% by weight.

As a result of thermal treatment of the precatalyst thus obtained at temperatures above 200 to 500° C., the binder escapes from the shell applied through thermal decomposition and/or combustion. Preference is given to effecting the thermal treatment in situ in the gas phase oxidation reactor.

The invention further provides a process for gas phase oxidation in which a gas stream comprising at least one hydrocarbon and molecular oxygen is passed through a catalyst which has been produced using an antimony trioxide having a senarmontite content of at least 20% by weight and where the senarmontite primary crystallites have a polymodal size distribution, wherein between 10% and 80% by weight have a primary crystallite size of <200 nm and a median primary crystallite size of <150 nm, preferably <100 nm, more preferably <50 nm.

A preferred embodiment of the invention is a process for gas phase oxidation of o-xylene and/or naphthalene to phthalic anhydride, in which a gas stream comprising at least o-xylene and/or naphthalene and molecular oxygen is passed through a catalyst system which comprises a plurality of catalyst zones arranged in succession in the reaction tube and which has been produced using an antimony trioxide having a senarmontite content of at least 20% by weight and where the senarmontite primary crystallites have a polymodal size distribution, wherein between 10% and 80% by weight have a primary crystallite size of <200 nm and a median primary crystallite size of <150 nm, preferably <100 nm, more preferably <50 nm.

EXAMPLES

Determination of primary crystallite sizes in the senarmontite content of the antimony trioxide: The primary crystallite size is understood to mean the maximum dimension of the primary crystallites averaged over the three spatial directions. The determination was effected by means of x-ray powder diffractometry. For this purpose, the antimony trioxide powder was analyzed in a Bruker "D8 Advance" x-ray powder diffractometer. The measurement parameters were as follows:

| Circle diameter | 500 mm |
| X-radiation | CuK-alpha ($\lambda = 1.54 \cdot 10^{-10}$ m) |
| Tube voltage | 40 kV |
| Tube current | 40 mA |
| Aperture | variable V20 |
| Collimator | variable V20 |
| Sol-X detector | |
| Detector aperture | 0.1 mm |
| Step width | 0.02° 2Θ |
| Step mode | continuous |
| Measurement time | 2.4 s/step |
| Measurement speed | 0.5° 2Θ/min |

In a Rietveld refinement of the powder diffractograms obtained with the Topas 4.2 software (TOPAS 4.2 User Manual, Bruker AXS GmbH, Karlsruhe), the crystalline senarmontite phase was inserted twice. At the start of the refinement, different primary crystallite sizes were set as start values (for example senarmontite with a primary crystallite size of 200 nm and senarmontite with a primary crystallite size of 10 nm). After convergence of the Rietveld refinement, in the case of a polymodal primary crystallite size distribution, several fractions and the corresponding median primary crystallite sizes are found, and the proportions thereof in the total senarmontite content can be read off quantitatively. In the case of a non-polymodal distribution, the senarmontite phases converge to give an identical primary crystallite size within the margin of error.

FIG. 1 shows an example of calculated and measured senarmontite peaks at 2 theta=27.7° in an x-ray powder diffractogram, and simulated values for primary crystallite sizes of 40 nm and >200 nm.

Production of a Four-Zone Catalyst System

Catalyst Zone CZ1:

2.94 g of cesium carbonate, 388.67 g of titanium dioxide (Fuji TA 100C, anatase, BET surface area 20 m$^2$/g), 166.57 g of titanium dioxide (Fuji TA 100, anatase, BET surface area 7 m$^2$/g), 43.47 g of vanadium pentoxide and 11.13 g of antimony trioxide (different type of antimony trioxide in each example) were suspended in 1587.96 g of demineralized water and stirred for 18 hours, in order to obtain a homogeneous distribution. To this suspension were added 93.1 g of organic binder, consisting of a copolymer of vinyl acetate and vinyl laurate in the form of a 50% by weight aqueous dispersion. In a fluidized bed apparatus, 820 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 9.1% by weight. The analyzed composition of the active material consisted of 7.1% by weight of V$_2$O$_5$, 1.8% by weight of Sb$_2$O$_3$, 0.38% by weight of Cs, remainder TiO$_2$.

Catalyst Zone CZ2:

2.40 g of cesium carbonate, 468.64 g of titanium dioxide (Fuji TA 100C, anatase, BET surface area 20 m$^2$/g), 76.32 g of titanium dioxide (Fuji TA 100, anatase, BET surface area 7 m$^2$/g), 48.67 g of vanadium pentoxide and 16.69 g of antimony trioxide (different type of antimony trioxide in each example) were suspended in 1587.96 g of demineralized water and stirred for 18 hours, in order to obtain a homogeneous distribution. To this suspension were added 93.1 g of organic binder, consisting of a copolymer of vinyl acetate and vinyl laurate in the form of a 50% by weight aqueous dispersion. In a fluidized bed apparatus, 765 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 8.5% by weight. The analyzed composition of the active material consisted of 7.95% by weight of V$_2$O$_5$, 2.7% by weight of Sb$_2$O$_3$, 0.31% by weight of Cs, remainder TiO$_2$.

Catalyst Zone CZ3:

0.77 g of cesium carbonate, 414.96 g of titanium dioxide (Fuji TA 100C, anatase, BET surface area 20 m²/g), 138.32 g of titanium dioxide (Fuji TA 100, anatase, BET surface area 7 m²/g), 43.47 g of vanadium pentoxide and 14.84 g of antimony trioxide (different type of antimony trioxide in each example) were suspended in 1587.96 g of demineralized water and stirred for 18 hours, in order to obtain a homogeneous distribution. To this suspension were added 88 g of organic binder, consisting of a copolymer of vinyl acetate and vinyl laurate in the form of a 50% by weight aqueous dispersion. In a fluidized bed apparatus, 775 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 8.5% by weight. The analyzed composition of the active material consisted of 7.1% by weight of $V_2O_5$, 2.4% by weight of $Sb_2O_3$, 0.09% by weight of Cs, remainder $TiO_2$.

Catalyst Zone CZ4:

8.04 g of ammonium hydrogenphosphate, 387.05 g of titanium dioxide (Fuji TA 100C, anatase, BET surface area 20 m²/g), 96.76 g of titanium dioxide (Fuji TA 100CT, anatase, BET surface area 27 m²/g) and 126.12 g of vanadium pentoxide were suspended in 1582.03 g of demineralized water and stirred for 18 hours, in order to obtain a homogeneous distribution. To this suspension were added 93.1 g of organic binder, consisting of a copolymer of vinyl acetate and vinyl laurate in the form of a 50% by weight aqueous dispersion. In a fluidized bed apparatus, 820 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 9.1% by weight. The analyzed composition of the active material consisted of 20% by weight of $V_2O_5$, 0.35% by weight of P, remainder $TiO_2$.

The catalytic oxidation of o-xylene to phthalic anhydride was conducted in a salt bath-cooled tubular reactor having an internal tube diameter of 25 mm and a length of 350 cm. From reactor inlet to reactor outlet, 130 cm of CZ1, 70 cm of CZ2, 60 cm of CZ3 and 60 cm of CZ4 were introduced. For temperature regulation, the tubular reactor was surrounded by a salt melt; a thermowell of external diameter 4 mm with an installed tensile element served for catalyst temperature measurement. An air flow of 4.0 m³ (STP)/h with loadings of 99 to 99.4% by weight o-xylene of 30 to 100 $g_{o\text{-}xylene}/m^3$ (STP)$_{air}$ was passed through the tubular reactor.

Example 1(Inventive)

The antimony trioxide used for CZ1, CZ2 and CZ3 was a material from Gredmann, Taiwan (batch number CAK111T2), which consisted of 99% by weight of senarmontite and 1% by weight of valentinite. These senarmontite primary crystallites feature a bimodal size distribution where 27% by weight have a primary crystallite size of <200 nm and a median primary crystallite size of 35 nm.

TABLE 1

Catalytic performance of the example 1 catalyst system at a total air flow rate of 4 m³ (STP)/h.

| Loading [$g_{o\text{-}X}/m^3$ (STP)$_{air}$] | Salt bath temperature [° C.] | $Y_{PA}{}^a$ [% by wt.] | $Y_{o\text{-}X}{}^b$ [% by wt.] | $Y_{PHD}{}^c$ [% by wt.] |
|---|---|---|---|---|
| 72.0 | 357.5 | 113.5 | 0.05 | 0.10 |
| 85.0 | 355.0 | 113.4 | 0.08 | 0.11 |
| 100.0 | 353.5 | 113.1 | 0.05 | 0.07 |

$^a$ PA yield
$^b$ o-xylene yield
$^c$ phthalide yield

Example 2(Inventive)

The antimony trioxide used for CZ1, CZ2 and CZ3 was a material from Gredmann, Taiwan (batch number B4K021T2), which consists of 78% by weight of senarmontite and 22% by weight of valentinite. These senarmontite primary crystallites feature a bimodal size distribution where 14% by weight have a primary crystallite size of <200 nm and a median primary crystallite size of 32 nm.

TABLE 2

Catalytic performance of the example 2 catalyst system at a total air flow rate of 4 m³ (STP)/h.

| Loading [$g_{o\text{-}X}/m^3$ (STP)$_{air}$] | Salt bath temperature [° C.] | $Y_{PA}{}^a$ [% by wt.] | $Y_{o\text{-}X}{}^b$ [% by wt.] | $Y_{PHD}{}^c$ [% by wt.] |
|---|---|---|---|---|
| 69.0 | 358.0 | 113.2 | 0.01 | 0.03 |
| 83.0 | 353.5 | 113.6 | 0.02 | 0.06 |
| 100.0 | 350.8 | 113.6 | 0.03 | 0.07 |

$^a$ PA yield
$^b$ o-xylene yield
$^c$ phthalide yield

Example 3(Inventive)

The antimony trioxide used for CZ1, CZ2 and CZ3 was a material from Gredmann, Taiwan (batch number CBK101T2), which consists of 67% by weight of senarmontite and 33% by weight of valentinite. These senarmontite primary crystallites feature a bimodal size distribution where 11% by weight have a primary crystallite size of <200 nm and a median primary crystallite size of 27 nm.

TABLE 3

Catalytic performance of the example 3 catalyst system at a total air flow rate of 4 m³ (STP)/h.

| Loading [$g_{o\text{-}X}/m^3$ (STP)$_{air}$] | Salt bath temperature [° C.] | $Y_{PA}{}^a$ [% by wt.] | $Y_{o\text{-}X}{}^b$ [% by wt.] | $Y_{PHD}{}^c$ [% by wt.] |
|---|---|---|---|---|
| 70.0 | 359.5 | 114.1 | 0.08 | 0.14 |
| 85.5 | 356.0 | 113.3 | 0.09 | 0.12 |
| 100.0 | 356.0 | 112.7 | 0.04 | 0.06 |

$^a$ PA yield
$^b$ o-xylene yield
$^c$ phthalide yield

Example 4(Non-Inventive)

The antimony trioxide used for CZ1, CZ2 and CZ3 was a material from Merck KGaA, Germany (batch number K40961235), which consists of 77% by weight of senarmontite and 23% by weight of valentinite. These senarmontite primary crystallites do not have a bimodal size distribution, but have a median primary crystallite size of 156 nm.

TABLE 4

Catalytic performance of the example 4 catalyst system at a total air flow rate of 4 m³ (STP)/h.

| Loading [$g_{o-X}$/m³ (STP)$_{air}$] | Salt bath temperature [° C.] | $Y_{PA}{}^a$ [% by wt.] | $Y_{o-X}{}^b$ [% by wt.] | $Y_{PHD}{}^c$ [% by wt.] |
|---|---|---|---|---|
| 74.0 | 358.0 | 112.8 | 0.09 | 0.18 |
| 86.0 | 357.0 | 112.5 | 0.07 | 0.13 |
| 100.0 | 354.0 | 112.2 | 0.09 | 0.14 |

$^a$ PA yield
$^b$ o-xylene yield
$^c$ phthalide yield

Example 5 (Non-Inventive)

The antimony trioxide used for CZ1, CZ2 and CZ3 was a material from Merck KGaA, Germany (batch number K43228935), which consists of 99% by weight of senarmontite and 1% by weight of valentinite. These senarmontite primary crystallites do not have a bimodal size distribution, but have a median primary crystallite size of >200 nm.

TABLE 5

Catalytic performance of the example 5 catalyst system at a total air flow rate of 4 m³ (STP)/h.

| Loading [$g_{o-X}$/m³ (STP)$_{air}$] | Salt bath temperature [° C.] | $Y_{PA}{}^a$ [% by wt.] | $Y_{o-X}{}^b$ [% by wt.] | $Y_{PHD}{}^c$ [% by wt.] |
|---|---|---|---|---|
| 72.0 | 357.0 | 111.5 | 0.03 | 0.06 |
| 85.0 | 350.0 | 112.6 | 0.12 | 0.13 |
| 94.0 | 348.0 | 111.9 | 0.10 | 0.10 |

$^a$ PA yield
$^b$ o-xylene yield
$^c$ phthalide yield

Production of a Five-Zone Catalyst System
Catalyst zone CZ1:
Preparation of the Vanadium Antimonate:

A thermostated jacketed glass vessel was initially charged with 5 L of demineralized water, and 1566.1 g of antimony trioxide from Gredmann, Taiwan (batch number CAK111T2) used, which consists of 99% by weight of senarmontite and 1% by weight of valentinite and wherein the senarmontite primary crystallites have a bimodal size distribution where 27% by weight have a primary crystallite size of <200 nm and a median primary crystallite size of 35 nm, were suspended therein by stirring at 90° C. for 18 hours. Then 2446.9 g of vanadium pentoxide and a further liter of demineralized water were added and the mixture was stirred at 90° C. for 25 hours. Thereafter, the suspension was cooled to 80° C. and dried by spray drying. The inlet temperature was 340° C., the outlet temperature 120° C. The spray powder thus obtained had a vanadium content of 32% by weight and an antimony content of 30% by weight.
Making Up the Suspension and Coating:

3.87 g of cesium carbonate, 349.69 g of titanium dioxide (Fuji TA 100CT, anatase, BET surface area 27 m²/g), 188.29 g of titanium dioxide (Fuji TA 100, anatase, BET surface area 7 m²/g), and 76.07 g of vanadium antimonate (synthesized as described above from Gredmann antimony trioxide (batch number CAK111T2) with 1% by weight of valentinite) were suspended in 1583 g of demineralized water and stirred for 18 hours, in order to obtain a homogeneous distribution. To this suspension were added 85 g of organic binder, consisting of a copolymer of vinyl acetate and vinyl laurate in the form of a 50% by weight aqueous dispersion. In a fluidized bed apparatus, 750 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 8.5% by weight. The analyzed composition of the active material consisted of 7.1% by weight of $V_2O_5$, 4.5% by weight of $Sb_2O_3$, 0.50% by weight of Cs, remainder $TiO_2$.
Catalyst Zone CZ2:

2.86 g of cesium carbonate, 427.54 g of titanium dioxide (Fuji TA 1000, anatase, BET surface area 20 m²/g), 127.71 g of titanium dioxide (Fuji TA 100, anatase, BET surface area 7 m²/g), 43.47 g of vanadium pentoxide and 11.13 g of antimony trioxide (material from Merck KGaA, Germany (batch number K40961235) having 77% by weight of senarmontite and 23% by weight of valentinite) were suspended in 1588 g of demineralized water and stirred for 18 hours, in order to obtain a homogeneous distribution. To this suspension were added 103 g of organic binder, consisting of a copolymer of vinyl acetate and vinyl laurate in the form of a 50% by weight aqueous dispersion. In a fluidized bed apparatus, 910 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 10% by weight. The analyzed composition of the active material consisted of 7.1% by weight of $V_2O_5$, 1.8% by weight of $Sb_2O_3$, 0.38% by weight of Cs, remainder $TiO_2$.
Catalyst Zone CZ3:

2.40 g of cesium carbonate, 468.67 g of titanium dioxide (Fuji TA 100C, anatase, BET surface area 20 m²/g), 76.29 g of titanium dioxide (Fuji TA 100, anatase, BET surface area 7 m²/g), 48.67 g of vanadium pentoxide and 16.69 g of antimony trioxide (material from Merck KGaA, Germany (batch number K40961235) having 77% by weight of senarmontite and 23% by weight of valentinite) were suspended in 1588 g of demineralized water and stirred for 18 hours, in order to obtain a homogeneous distribution. To this suspension were added 88 g of organic binder, consisting of a copolymer of vinyl acetate and vinyl laurate in the form of a 50% by weight aqueous dispersion. In a fluidized bed apparatus, 770 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 8.5% by weight. The analyzed composition of the active material consisted of 7.95% by weight of $V_2O_5$, 2.7% by weight of $Sb_2O_3$, 0.31% by weight of Cs, remainder $TiO_2$.
Catalyst Zone CZ4:

0.77 g of cesium carbonate, 414.96 g of titanium dioxide (Fuji TA 100C, anatase, BET surface area 20 m²/g), 138.32 g of titanium dioxide (Fuji TA 100, anatase, BET surface area 7 m²/g), 43.47 g of vanadium pentoxide and 14.84 g of antimony trioxide (material from Merck KGaA, Germany (batch number K40961235) having 77% by weight of senarmontite and 23% by weight of valentinite) were suspended in 1588 g of demineralized water and stirred for 18 hours, in order to obtain a homogeneous distribution. To this suspension were added 88 g of organic binder, consisting of a copolymer of vinyl acetate and vinyl laurate in the form of a 50% by weight aqueous dispersion. In a fluidized bed apparatus, 775 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 8.5% by weight. The analyzed composition of the active material consisted of 7.1% by weight of $V_2O_5$, 2.4% by weight of $Sb_2O_3$, 0.09% by weight of Cs, remainder $TiO_2$.

Catalyst zone CZ5:

8.04 g of ammonium hydrogenphosphate, 387.05 g of titanium dioxide (Fuji TA 100C, anatase, BET surface area 20 m$^2$/g), 96.76 g of titanium dioxide (Fuji TA 100CT, anatase, BET surface area 27 m$^2$/g) and 126.12 g of vanadium pentoxide were suspended in 1582 g of demineralized water and stirred for 18 hours, in order to obtain a homogeneous distribution. To this suspension were added 93 g of organic binder, consisting of a copolymer of vinyl acetate and vinyl laurate in the form of a 50% by weight aqueous dispersion. In a fluidized bed apparatus, 820 g of this suspension were sprayed onto 2 kg of steatite (magnesium silicate) in the form of rings having dimensions of 7 mm×7 mm×4 mm and dried. After the catalyst had been calcined at 450° C. for one hour, the active material applied to the steatite rings was 9.1% by weight. The analyzed composition of the active material consisted of 20% by weight of $V_2O_5$, 0.35% by weight of P, remainder $TiO_2$.

The catalytic oxidation of o-xylene to phthalic anhydride was conducted in a salt bath-cooled tubular reactor having an internal tube diameter of 25 mm and a length of 350 cm. From reactor inlet to reactor outlet, 80 cm of CZ1, 60 cm of CZ2, 70 cm of CZ3, 50 cm of CZ4 and 60 cm of CZ5 were introduced. For temperature regulation, the tubular reactor was surrounded by a salt melt; a thermowell of external diameter 4 mm with an installed tensile element served for catalyst temperature measurement. An air flow of 4.0 m$^3$ (STP)/h with loadings of 99 to 99.4% by weight o-xylene of 30 to 100 g$_{o\text{-}xylene}$/m$^3$ (STP)$_{air}$ was passed through the tubular reactor.

Example 6(Inventive)

For the vanadium antimonate synthesis of CZ1, the antimony trioxide from Gredmann, Taiwan (batch number CAK111T2) was used, which consists of 99% by weight of senarmontite and 1% by weight of valentinite. These senarmontite primary crystallites feature a bimodal size distribution where 27% by weight have a primary crystallite size of <200 nm and a median primary crystallite size of 35 nm. The antimony trioxide used for CZ2, CZ3 and CZ4 was a material from Merck KGaA. Germany (batch number K40961235), which consists of 77% by weight of senarmontite and 23% by weight of valentinite. These senarmontite primary crystallites do not have a bimodal size distribution, but have a median primary crystallite size of 156 nm.

TABLE 6

Catalytic performance of the example 6 catalyst system at a total air flow rate of 4 m$^3$ (STP)/h.

| Loading [g$_{o\text{-}X}$/m$^3$ (STP)$_{air}$] | Salt bath temperature [° C.] | Y$_{PA}$$^a$ [% by wt.] | Y$_{o\text{-}X}$$^b$ [% by wt.] | Y$_{PHD}$$^c$ [% by wt.] |
|---|---|---|---|---|
| 72.0 | 364.0 | 112.8 | 0.02 | 0.07 |
| 83.0 | 356.0 | 113.0 | 0.03 | 0.07 |
| 100.0 | 349.0 | 113.9 | 0.05 | 0.08 |

$^a$ PA yield
$^b$ o-xylene yield
$^c$ phthalide yield

Example 7(Non-Inventive)

For the vanadium antimonate synthesis of CZ1, the antimony trioxide from Merck KGaA, Germany (batch number K43228935) was used, which consists of 99% by weight of senarmontite and 1% by weight of valentinite. These senarmontite primary crystallites do not have a bimodal size distribution, but have a median primary crystallite size of >200 nm. For CZ2, CZ3 and CZ4, an antimony trioxide from Merck KGaA, Germany (batch number K40961235) was used, which consists of 77% by weight of senarmontite and 23% by weight of valentinite. These senarmontite primary crystallites do not have a bimodal size distribution, but have a median primary crystallite size of 156 nm.

TABLE 7

Catalytic performance of the example 7 catalyst system at a total airflow rate of 4 m$^3$ (STP)/h.

| Loading [g$_{o\text{-}X}$/m$^3$ (STP)$_{air}$] | Salt bath temperature [° C.] | Y$_{PA}$$^a$ [% by wt.] | Y$_{o\text{-}X}$$^b$ [% by wt.] | Y$_{PHD}$$^c$ [% by wt.] |
|---|---|---|---|---|
| 73.0 | 368.0 | 111.6 | 0.06 | 0.16 |
| 85.0 | 361.0 | 112.5 | 0.06 | 0.12 |
| 100.0 | 349.5 | 113.3 | 0.03 | 0.08 |

$^a$ PA yield
$^b$ o-xylene yield
$^c$ phthalide yield

TABLE 8

Summary of relevant properties of the antimony trioxides used

| Example | Company | Batch number | Senarmontite content | Senarmontite content with primary crystallite size <200 nm, median primary crystallite size | Senarmontite content with primary crystallite size >200 nm, median primary crystallite size | Valentinite content | Purity (%) |
|---|---|---|---|---|---|---|---|
| 1, 6 | Gredmann | CAK111T2 | 99% by weight | 27% by weight, 35 nm | 72% by weight, >200 nm | 1% by weight | 99.7 |
| 2 | Gredmann | B4K021T2 | 78% by weight | 14% by weight, 32 nm | 64% by weight, >200 nm | 22% by weight | 99.8 |
| 3 | Gredmann | CBK101T2 | 67% by weight | 11% by weight, 27 nm | 56% by weight, >200 nm | 33% by weight | 99.7 |

TABLE 8-continued

Summary of relevant properties of the antimony trioxides used

| Example | Company | Batch number | Senarmontite content | Senarmontite content with primary crystallite size <200 nm, median primary crystallite size | Senarmontite content with primary crystallite size >200 nm, median primary crystallite size | Valentinite content | Purity (%) |
|---|---|---|---|---|---|---|---|
| 4, 6, 7 | Merck KGaA | K40961235 | 77% by weight | 156 nm | | 23% by weight | 99.8 |
| 5, 7 | Merck KGaA | K43228935 | 99% by weight | | >200 nm | 1% by weight | 99.6 |

The invention claimed is:

1. A catalyst system comprising a plurality of catalyst zones is arranged in succession in the reaction tube, which is produced using an antimony trioxide having a senarmontite content of at least 20% by weight and where the senarmontite primary crystallites have a polymodal size distribution, wherein between 10% and 80% by weight have a primary crystallite size of <200 nm and a median primary crystallite size of <150 nm.

2. The catalyst according to claim 1, wherein an antimony trioxide having a senarmontite content of at least 50% by weight is used.

3. A catalyst system comprising a plurality of catalyst zones is arranged in succession in the reaction tube, which is produced using an antimony trioxide having a senarmontite content of at least 20% by weight and where the senarmontite primary crystallites have a polymodal size distribution, wherein between 10% and 80% by weight have a primary crystallite size of <200 nm and a median primary crystallite size of <150 nm and, wherein the senarmontite primary crystallites have a bimodal size distribution.

4. The catalyst according to claim 1, wherein between 10% and 80% by weight of the senarmontite primary crystallites have a primary crystallite size of <200 nm and a median primary crystallite size of <100 nm.

5. The catalyst according to claim 1, wherein between 10% and 50% by weight of the senarmontite primary crystallites have a primary crystallite size of <200 nm and a median primary crystallite size of <150 nm.

6. The catalyst according to claim 1, wherein between 10% and 50% by weight of the senarmontite primary crystallites have a primary crystallite size of <200 nm and a median primary crystallite size of <100 nm.

7. A process for gas phase oxidation in which a gas stream comprising at least one hydrocarbon and molecular oxygen is passed through the catalyst according to claim 1.

8. The process according to claim 7, wherein the hydrocarbon is o-xylene and/or naphthalene.

9. A process for gas phase oxidation of o-xylene and/or naphthalene to phthalic anhydride, in which a gas stream comprising at least o-xylene and/or naphthalene and molecular oxygen is passed through the catalyst according to claim 1.

10. The catalyst according to claim 1, wherein between 10% and 80% by weight of the senarmontite primary crystallites have a primary crystallite size of <200 nm and median primary crystallite size of <50 nm.

* * * * *